United States Patent [19]
Rokitowski

[11] Patent Number: 5,750,127
[45] Date of Patent: May 12, 1998

[54] COLOR COSMETIC COMPOSITION CONTAINING ALCOHOL MODIFIED WAX

[75] Inventor: Karen Lee Rokitowski, Beacon, N.Y.

[73] Assignee: Elizabeth Arden, a Division of Conopco, Inc., New York, N.Y.

[21] Appl. No.: 795,096

[22] Filed: Feb. 5, 1997

Related U.S. Application Data

[63] Continuation-in-part of Ser. No. 616,793, Mar. 15, 1996.

[51] Int. Cl.$^6$ .............................. A61K 7/00; A61K 7/021
[52] U.S. Cl. ........................ 424/401; 424/63; 424/70.7; 514/787
[58] Field of Search .................... 424/63, 70.7, 401, 424/494; 514/787

[56] References Cited

U.S. PATENT DOCUMENTS

| | | | |
|---|---|---|---|
| Re. 29,871 | 12/1978 | Papantoniou et al. | 424/64 |
| 3,937,811 | 2/1976 | Papantoniou et al. | 424/64 |
| 4,871,536 | 10/1989 | Arraudeau et al. | 424/59 |
| 5,053,220 | 10/1991 | Arraudeau et al. | 424/63 |
| 5,176,902 | 1/1993 | Castro et al. | 424/63 |
| 5,356,627 | 10/1994 | Da Cunha et al. | 424/401 |
| 5,389,363 | 2/1995 | Snyder et al. | 424/70.7 |
| 5,460,808 | 10/1995 | Mausner | 424/70.7 |
| 5,531,986 | 7/1996 | Shevade et al. | 424/68 |

FOREIGN PATENT DOCUMENTS

58/092605 6/1983 Japan.

OTHER PUBLICATIONS

Cosmetics & Toiletries, (Aug. 1990) "A New Beeswax Derivative for Cosmetic Formulations", vol. 105, pp. 53–56, 58–60 and 62.

MST for Koster Kuenen.

*Primary Examiner*—Thurman K. Page
*Assistant Examiner*—Sharon Howard

[57] ABSTRACT

A color mascara composition comprising from about 1 to about 99 wt. % of a natural wax modified with a $C_1$–$C_{60}$, preferably a $C_{20}$–$C_{40}$ alkanol to substantially esterify $C_{12}$–$C_{60}$ free fatty acids of the wax to form an esterified wax; from about 0.001 to about 20 wt. % of a colorant; and an effective of a cosmetically acceptable carrier.

14 Claims, No Drawings

5,750,127

COLOR COSMETIC COMPOSITION CONTAINING ALCOHOL MODIFIED WAX

This is a continuation-in-part application of Ser. No. 08/616,793, filed Mar. 15, 1996.

FIELD OF THE INVENTION

The present invention relates to a cosmetic composition containing a wax esterified with an alcohol and mixed with an emulsion system. In particular, the invention relates to a color cosmetic composition which is useful for various applications to skin and hair, especially applications to eyelashes and eyebrows such as mascara.

BACKGROUND OF THE INVENTION

Cosmetic compositions used for making up eyelashes, such as mascara, are generally based on waxes which provide an important structurant function (see U.S. Pat. No. 5,053,220 issued to L'Oreal). However it has been noted that when waxes are used alone in mascara compositions, non-homogeneous films are formed on the eyelashes which lead to drying and is noticed by the consumers in the form of brittle flakes. Id. To address this disadvantage, prior art formulators have included thickening agents, such as hydroxyethylcellulose and emulsifying agents which can affect the stability of the compositions.

Additionally, colorants present in the compositions used to define the presence of lashes may adversely react with $C_2$–$C_{16}$ fatty acids present in the compositions to form crystals which cause the compositions to lose stability. While fatty acids are not often purposely formulated with color cosmetic compositions these materials are often present as substantial impurities in standard waxes such as candelilla, ozokerite, carnauba, beeswax, lanolin and spermaceti waxes (see U.S. Pat. No. 5,176,902 issued to Elizabeth Arden).

Natural beeswax is one of the most popular cosmetic ingredients because of its emulsifying and consistency regulating properties. Beeswax is also one of the few natural emulsifiers available to the cosmetic chemist. See Rit, A. W. et al., "A New Beeswax Derivative for Cosmetic Formulations", Cosmetics and Toiletries, Vol. 105, No. 8, pp. 53–62.

To improve the performance of beeswax, the free fatty acids of the wax have been esterified with short and medium chain alcohols such as cetyl, stearyl and isostearyl alcohols as described in JP 5892605 assigned to Noda Wax KK (1983), Chem. Abs. 99:93 510y (1982). Natural beeswax has also been modified to form a more hydrophilic type. See Rit, A. W. Supra at page 53. However such modified beeswax is not recommended to replace natural unmodified beeswax in cosmetic formulas because of other advantages that natural beeswax provides to the formulation. (See Rit et al. Supra at page 58).

There therefore exists a need for an improved color cosmetic composition which is long lasting, easy to apply and effective in lengthening and thickening eyelashes of the wearer without undereye smudging.

Another object of the invention is to provide a color cosmetic composition, especially a mascara, that can be rendered reproducibly stable in a cost effective method.

A further object of the invention is to provide a color cosmetic composition formulated with colorants that will have good color impact while maintaining the stability of the composition itself.

SUMMARY OF THE INVENTION

The present invention meets these and other objects by providing a color cosmetic mascara composition comprising:

a) from about 0.001 to about 20 wt. % of a colorant;

b) from about 1 to about 99% of a natural wax, preferably beeswax, modified with a $C_1$–$C_{60}$ alkanol to substantially esterify substantially all free fatty acids of the wax; and c) a cosmetically acceptable carrier.

In another aspect of the invention, a method has been devised for manufacturing color cosmetic compositions useful for mascara which comprises:

a) selecting a natural wax that has been esterified with a $C_1$–$C_{60}$ alcohol to substantially convert $C_{12}$–$C_{60}$–fatty acids present in the beeswax into esters to form an esterified wax;

b) mixing about 1 to about 99% of the esterified wax with a colorant in an amount of from about 0.001 to about 20%; and c) forming a color cosmetic mascara with a mixture from step (b).

DETAILED DESCRIPTION OF PREFERRED EMBODIMENTS

It has been unexpectedly discovered that a natural wax conventionally used as a base in mascara compositions may be replaced with a wax esterified with a molar equivalent of more of a $C_1$–$C_{60}$ mono- or polyhydric alcohol, preferably a $C_{20}$–$C_{40}$ monohydric alcohol, most preferably a $C_{20}$–$C_{35}$ monohydric alcohol. The alcohol modifies the $C_{12}$–$C_{60}$ free fatty acid impurities present in the wax to form an esterified wax which is free, or substantially free of this impurity. A moler equivalent of one or more moles of the alcohol may be combined with the wax to produce the esterified form.

Particularly preferred are the $C_{20}$–$C_{40}$ monohydric alcohols, especially preferred are the $C_{20}$–$C_{35}$ monohydric alcohols. Illustrative alcohols useful in the invention include behenyl, hexanediol behenyl and mixtures thereof.

The esterification process involves combining the natural wax with from 0.5 to 20% of the alcohol in a vessel under agitation at a temperature of from about 40° C. to about 250° C., preferably from about 80° C. to about 150° C.

Advantageously, a vacuum is applied to the vessel to remove water vapor formed in the esterification. An effective amount of an acid catalyst may be employed, for instance, a mineral acid (e.g. sulfuric or hydrochloric acid), an organic acid (e.g. toluene sulphono acid) or an inorganic substance, such as boron trifluoride etherate.

The natural waxes which may be suitably modified for the invention are low melting organic compounds of high molecular weight which are solid at room temperature. Among the natural waxes which are useful are those of animal origin which include beeswax, spermaceti, lanolin, and shellac wax or those of vegetable origin which include carnauba, candelilla, bayberry and sugar cane wax. Preferred waxes are beeswax, candelilla, carnauba, lanolin and spermaceti waxes. Most preferred is beeswax.

Commercial suppliers of such esterified waxes include Unichema North America of Chicago, Ill. and Koster Keunen, Inc.

The amount of the alkanol modified wax in the composition may range from about 1 to about 99% by weight, preferably from about 1 to about 30% by weight, optimally between about 1 and about 20% by weight.

The alkanol modified wax is substantially free or is free of such fatty acids in the compounds after the esterification process. The maximum amount of free fatty acids which may remain in the waxes would be expected to be less than 1% by weight.

Colorants and Pigments

Cosmetically acceptable colorants for imparting color to eyelashes or eyebrows in the present invention includes, but are not limited to, iron oxides (black, red and yellow); ultra marine blue, ferric ammonium ferrocyanide, carmine, manganese violet, ultra marine pink, ultramarine violet, chromium hydroxide green, chromium oxide green, titanium dioxide, organic lakes such as D&C Blue #1, D&C Yellow #5, D&C Red #40, D&C Green #5 and the like. It should also be noted that any combination of colorants may be used in the present composition.

The amount of colorant or pigment should range from about 0.001 to about 20% by weight of the composition. The preferable range is from about 0.1 to about 15%, optimally from about 2 to about 15% by weight. Particularly preferred colorants are the iron oxides and the organic lake colorants.

Pigment Dispersants

The composition preferably contains a dispersant to disperse the pigments or colorants thoroughly the product. Such disperants include a polyhydroxystearic acid supplied by ICI under the trademark Arlacel® octyldodecyl myristate triisocetyl citrate supplied by Bernel Chemical Co., 12-hydroxystearic acid 2-octadeconal supplied by Alzo, Inc. The dispersant is present in the composition in an amount of from about 0.1 to about 5 wt. %, preferably about 0.5 wt. % to about 2 wt. %.

Cosmetically Acceptable Carrier

When the mascara is aqueous in form (generally in the form of an oil-in-water emulsion) it contains preferably from about 50 to about 70% by weight of water with respect to the total weight of the mascara. On the other hand when the mascara is anhydrous, it contains a volatile component in an amount generally between 35 to abut 50% to the total weight of the mascara. Volatile components which may be useful include isoparaffin, oil of turpentine, isopropyl alcohol, ethyl alcohol, white spirits and the like.

Emulsifier Components

The emulsifier component serves to both solubilize the water soluble and non-water soluble phases of the compositions, and also serves as an emollient to provide a pleasant, aesthetically pleasing tactile feeling to the skin. The emulsifier should be present in an amount sufficient to combine the two phases of the composition.

Preferably, the emulsifier component comprises at least one emulsifier selected from the group consisting of triethanolamine, a glyceryl ester and a carboxylic $C_2$–$C_{20}$ fatty acid.

The glyceryl ester is preferably selected from the group consisting of glycerol stearate, glycerol palmitate, glycerol arachidate and mixtures thereof. Most preferably, the glycerol ester is glycerol stearate.

The $C_{12}$–$C_{20}$ fatty acid is preferably selected from the group of stearic acid, isostearic acid and mixtures thereof.

Preferably, the emulsifier components comprises glycerol stearate, triethanolamine, isostearic acid and stearic acid. Most preferably, the glycerol stearate comprises from about 0.1 to about 4% of the composition and the triethanolamine comprises from about 0.5 to about 5% of the composition. The stearic acid should be present in amounts less than about 5% of the composition, preferably 3% and less.

Natural waxes which are hydrophically modified may also be present as emulsifier in amounts less than about 3 wt. %, preferably less than about 2 wt. %. Particularly preferred are natural waxes of animal origin which have been modified with a sorbitan ester such as polyethylene glycol sorbitan beeswax.

It is also preferable to include certain large molecular weight acrylate copolymers (i.e., 20–40,000 MW). Such copolymers are those supplied under the tradename Carboset (i.e., MW=30,000) supplied by B.F. Goodrich. The copolymer should be present in an amount of from about 0.5 to about 5 wt. %, preferably 1 to about 4 wt. %.

The emulsifier system should be present in amounts of less than about 15% of the composition, preferably 0.1 to 10 wt. %.

Thickeners

The thickener component is included in the composition in an amount sufficient to retain the composition when it is supplied through the eyelashes of a wearer. The thickener component can comprise at least one thickener selected from the group consisting of cellulose derivatives and acacia (also known as gum arabic). Preferably the thickener components include sodium alginate and cellulose derivatives such as hydroxyethyl cellulose, hydroxymethyl cellulose, hydroxypropyl cellulose and hydroxypropy methyl cellulose. The compositions can also be thickened using a mixture of polyethylene glycol and polyethylene glycerol stearate or distearate or a mixture of phosphoric acid esters and fatty amides. The thickener should be present in the composition in an amount from about 0.1 to 5 wt. %, preferably 0.5 to 3 wt. %.

Preservative

The preservative is included in the composition to prevent the growth of any microbes in the mascara composition. The preservative is present in a quantity position to prevent microbial growth in a composition, preferably in an amount from about 0.01% to about 2 wt. % of the composition, preferably 0.4 to about 1.5 wt. %.

The preservative includes at least one of the following preservatives: propylparaben, methylparaben, phenoxyethanol, ethylparaben, butylparaben, EDTA, imidizolidinyl urea, diazolidnyl urea and mixtures thereof.

Film Formers

The film former may be included to adhere to looks to aid in the prevention of any smudging.

Film formers are present in an amount of from about 0.1 to about 10 wt. %.

The film former includes at least one of the following compounds: polyvinylpyrolidone (PVP), modified polyvinylpyrolidone and mixtures thereof such as PVP, polycarbamyl pyrolidone polyglycol ester and water.

Vitamin Components

The vitamin component comprises at least one vitamin selected from the group consisting of fatty acid esters of ascorbic acids (Vitamin C) and their derivatives, tocopherol esters (Vitamin E) and their derivatives, and panthenol and its derivatives. Panthenol is the racemic di-form of 2,4 dihydroxy-N-(3-hydroxypropyl )-3,3–dimethylbutanamide and is also known as Vitamin B5.

Preferably the fatty acid esters of ascorbic acid is selected from the group consisting of ascorbyl palmitate, ascorbyl myristate, ascorbyl stearate and mixtures thereof. Most preferably, the fatty acid ester of ascorbic acid is ascorbyl palmitate.

Preferably, the tocopherol esters are selected from the group consisting of tocopherol acetate, tocopherol propionate, tocopherol butyrate and mixtures thereof. Most preferably the tocopherol ester is tocopherol acetate.

Preferably the vitamin component comprises ascorbic palmitate, tocopherol acetate, panthenol or mixtures thereof.

The vitamin component is present in the composition in an amount from about 0.01 wt. % to about 0.5 wt. %, preferably 0.05 wt. % to about 0.25 wt. %.

Protein Component

The protein component comprises at least one protein selected from the group of silk powder, keratin and mixtures thereof. Preferably, the component is present in an amount of from 0.5% to about 5 wt. % of the composition.

Ceramide Component

Phytosphingosine-containing ceramides which may also be included in the invention have the following formula (1):

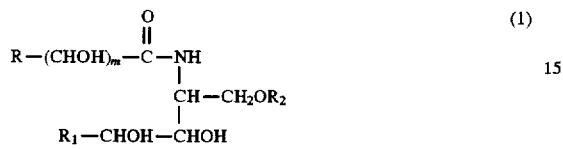

wherein R represents a linear or branched saturated or unsaturated, hydroxylated or non-hydroxylated aliphatic hydrocarbon group having from 1 to 49 carbon atoms or a subgroup (2):

$R_1$ represents a linear or branched, saturated or unsaturated, hydroxylated or non-hydroxylated aliphatic hydrocarbon group having from 8 to 28 carbon atoms;

$R_2$ represents H, a phosphate residue, a sulphate residue, or a sugar residue:
 a is an integer of from 7 to 50
 b is an integer of from 10 to 100
 m is 0 or 1

Y represents H or a residue of a $C_{14}$–$C_{22}$ fatty acid having the general structure (3):

where
z is —OH or an epoxy oxygen
x is an integer of from 12 to 20
y is an integer of from 20 to 40
z is 0 or an integer of from 1 to 4.

With reference to structure (1), the group R preferably represents an aliphatic hydrocarbon group having from 12 to 30 carbon atoms or the group Y—O—($C_a$ $H_b$)—; while the group $R_1$ preferably represents an aliphatic hydrocarbon group having from 12 to 22 carbon atoms.

With reference to structure (2), the value of "a" is preferably an integer of from 24 to 30 and the value of "b" is preferably an integer of from 44 to 60.

Also, with reference to structure (2), the group Y preferably represents a straight chain saturated $C_{16}$–$C_{18}$ fatty acid residue or a straight chain all cis n-6,9 di-unsaturated $C_{16}$–$C_{18}$ fatty acid residue.

Specific examples of these phytosphingosine-containing ceramides are those having the structures (4) to (16):

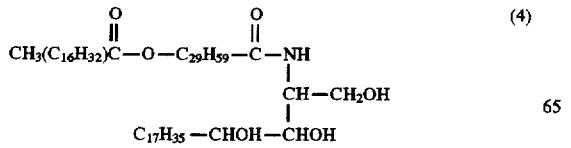

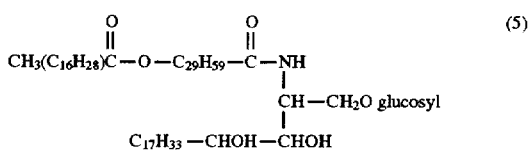

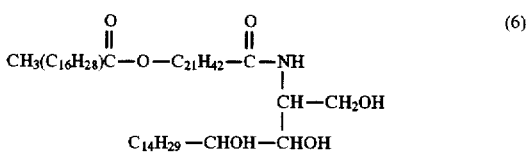

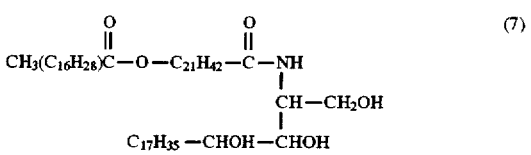

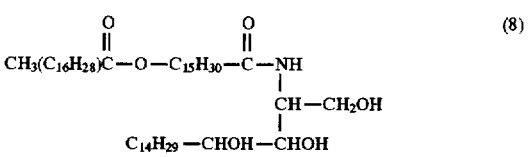

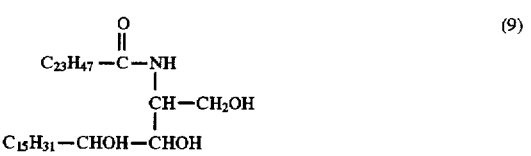

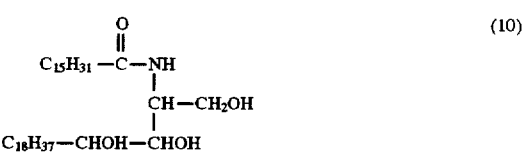

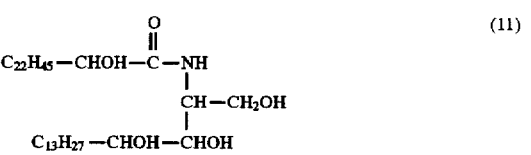

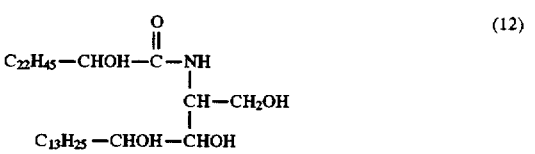

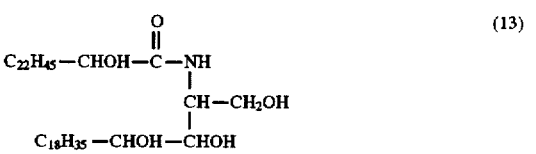

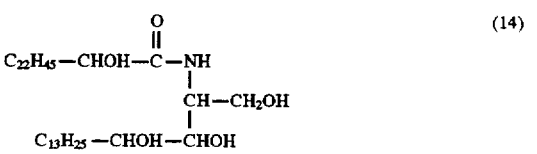

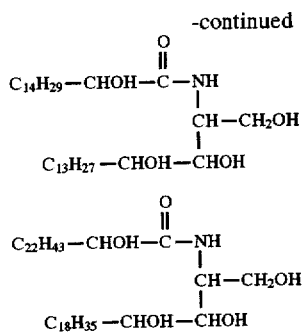

The phytosphingosine-containing ceramide may be present in the composition according to the invention is from 0.00001 to 2%, preferably from 0.001 to 1%, optimally from 0.01 to 0.1% by weight.

The most preferred ceramides are Ceramide 3 referred to as N-stearoyl-phytosphingosine or stearoyl hydroxysphinganine and Ceramide 6 referred to as 2-hydroxy.

Optional Ingredients

Optional ingredients which are preferably included in the composition include an antioxidant component; a film forming agent; and a filler.

Filler ingredients include talc, etc. Film forming agents include dimethicone copolymers, etc. Each optional ingredient is present in the composition in an amount up to about 2 wt. %, preferably up to about 1 wt. %.

Preparation

A preferred mascara composition according to the present invention comprises water and the following ingredients emulsified and dispersed in the water:

a) about 1 to about 20 wt. % of a natural beeswax modified with a $C_1$–$C_{60}$ preferably $C_{20}$–$C_{40}$ alkanol to substantially esterify free fatty acids of the beeswax;

b) about 0.5 to about 2.0 wt. % of triethanolamine;

c) about 0.1 to about 2.0 wt. % of a preservative selected from a group consisting of methylparaben, ethylparaben, propylparaben, imidazolidinyl urea, diazolidinyl urea and mixtures thereof;

d) about 0.01 to about 0.1 wt. % of panthenol;

e) about 0.05 to about 2 wt. % of hydroxyethylcellulose;

f) about 0.001 to about 1wt. % of talc;

g) about 1 wt. % to about 2 wt. % of stearic acid;

h) about 0.5 to about 1 wt. % of glyceryl stearate;

i) about 2 to about 8 wt. % of acrylate copolymer;

j) about 1.0 to about 2.0 wt. % of Peg-20-sorbitan beeswax;

k) about 0.1 to about 1.0% of dimethicone copolymer;

l) about 2 to about 5 wt. % of carnauba wax;

m) about 0.5 to about 15 wt. % iron oxides;

n) about 0.5 to about 2 wt. % isostearic acid;

o) about 0.1 to about 5 wt. % organic lake colorants;

p) about 0.1 to about 10 wt. % of a film former selected from the group consisting of polyvinylpyrolidone (PVP), modified PVP and mixtures thereof;

q) about 0.5 to about 2 wt. % of a polyhydroxystearic acid.

The mascara compositions of the present invention can be prepared by blending together the ingredients described above. A black mascara was prepared according to the following procedure in a suitable mixing vessel equipped with a homogenizer or suitable agitation. The hydroxyethyl cellulose was mixed in deionized water. The mixture was then heated and the copolymer, methylparaben and pigments were added. The mixture temperature was subsequently increased from about 85° C. to about 900° C. to begin the emulsification process. The triethanolamine, the alkanol esterified beeswax, the Peg-20 -sorbitan beeswax, the carnauba wax, the propylparaben, the stearic acid and isostearic acid were added to the heated mixture with agitation until a homogeneous phase was obtained. The mixture was then cooled as mixing continued until the components were completely dispersed in the water. The remaining ingredients were added with mixing and the emulsified mixture was then cooled to about 40° C. and batches were transferred for packaging.

EXAMPLE 1.

The following formulation containing behenyl beeswax according to the invention was prepared:

| Ingredient vs. % Weight | |
|---|---|
| Behenyl beeswax | 17.4 wt. % |
| Deionized water | 52.5% |
| Hydroxyethylcellulose | 1.0% |
| Iron oxide (black) | 8.1% |
| Methyl paraben and propyl paraben | 0.5% |
| Triethanolamine | 1.5% |
| Isostearic acid | 1.0% |
| Stearic acid | 2.0% |
| Glyceryl stearate | 0.6 |
| Peg-20-sorbitan beeswax | 1.5% |
| Talc | 0.90% |
| Urea | 0.2% |
| Panthenol | 0.05% |
| Acrylate copolymer | 3.5%[1] |
| Dimethicone copolymer | 0.3% |
| EDTA | 0.1% |
| Carnauba wax | 3.15% |
| PVP | 1.0% |
| PVP/polycarbamyl polyglycol ester mixture[2] | 4.0% |
| Polyhydroxystearic acid | 1.00% |

[1] supplied as Carboset by B. F. Goodrich
[2] supplied as Pecogel H-12 by Phoenix Chemical The mascara composition was prepared as described above.

Example 2.

A prior art mascara composition containing 18.8 wt. % natural yellow beeswax supplied by Stahl and Pitsch rather than the behenyl beeswax of the invention was prepared as described in Example 1.

The stabilities of the inventive composition and the prior art composition were compared by measuring the viscosities of the samples using a Brookfield Viscometer, T. F. spindle at 4 rpms after storage for at least one month at room temperature, 37° C. and at alternating temperatures.

Alternating temperatures were achieved by storing the samples and increasing temperatures in 5° C. increments from room temperature to 43° C. in 12 hours. The temperatures were then decreased 5° C. over the next 12 hours from 43 C. to 5° C. The alternating temperature test provides the most severe test conditions for the mascara compositions.

The following viscosity reading in centiposes were obtained:

TABLE 2

| | Behenyl beeswax | | |
|---|---|---|---|
| Time | Room Temperature | 37° C. | Alternating Temperature |
| Initial | 47,500 | 47,500 | 47,500 |
| 24 hours | 30,000 | 30,000 | 30,000 |
| 1 week | 75,000 | 107,500 | 167,500 |
| 2 weeks | 81,250 | 81,250 | 165,000 |
| 3 weeks | 78,750 | 77,500 | 128,750 |
| 1 month | 67,500 | 107,500 | 162,500 |

It was observed that the mascara composition of the invention was substantially more stable than the prior art composition. An acceptable viscosity was achieved after about 1 week and this viscosity was maintained. In contrast, the prior art composition continued to thicken in storage to unacceptable levels.

Without being limited by theory, it is believed that crystal poisons were formed in the prior art composition because of the presence of the free fatty acids of the yellow beeswax. By replacing the natural beeswax with an esterified beeswax, the crystal poisons were not formed and the inventive product was substantially more stable.

TABLE 3

| | Natural Yellow Beeswax Containing Composition | | |
|---|---|---|---|
| Time | Room Temperature | 37° C. | Alternating Temperature |
| Initial | 74,370 | 74,370 | 74,370 |
| 24 hours | 108,120 | 108,120 | 108,120 |
| 1 week | 103,750 | 137,500 | 180,000 |
| 2 weeks | 132,500 | 148,750 | 208,750 |
| 3 weeks | 130,000 | 141,250 | 212,500 |
| 1 month | 130,000 | 140,000 | 226,250 |

What is claimed:

1. A color mascara composition comprising:
    a) from about 1 to about 99 wt. % of a natural wax modified with a $C_{20}$–$C_{60}$ alkanol to substantially esterify $C_{12}$–$C_{60}$ free fatty acids of the wax to form an esterified wax;
    b) from about 0.001 to about 20 wt. % of a colorant; and
    c) an effective amount of a cosmetically acceptable carrier to deliver active ingredients of the composition,
the composition being substantially stable after four weeks in storage at room temperature.

2. The color mascara composition according to claim 1 wherein the wax is selected from the group consisting of behenyl beeswax, hexanediol behenyl beeswax and mixtures thereof.

3. The color mascara composition according to claim 1 wherein the wax is present in an amount from about 1 to about 20 wt. %.

4. The color mascara composition according to claim 1 wherein the colorant is selected from the group consisting of iron oxides, ultra marine blue, ferric ammonium ferrocyanide, carmine, manganese violet, ultra marine pink, ultra marine violet, chromium hydroxide green, chromium oxide green, titanium dioxide, organic lakes and mixtures thereof.

5. The color mascara composition according to claim 1 wherein the cosmetically acceptable carrier is selected from the group consisting of water, a solvent and mixtures thereof.

6. The color mascara composition according to claim 1 wherein the composition further comprises an emulsifier component selected from the group consisting of triethanolamine, glyceryl ester, an acrylate copolymer, a carboxylic $C_{12}$–$C_{20}$ fatty acid and mixtures thereof.

7. A composition according to claim 1 further comprising a vitamin component in an amount from about 0.01 to about 0.05 wt. %.

8. A composition according to claim 1 further comprising a thickener component.

9. A composition according to claim 1 further selected from the group consisitng of a polyvinylpyrolidone modified polyvinylpyrolidone and mixtures thereof.

10. A method for preparing a mascara composition comprising:
    a) selecting a natural wax that has been esterified with a $C_{20}$–$C_{60}$ mono or polyhydric alcohol to substantially convert $C_{20}$–$C_{60}$ fatty acids of the wax into respective esters to form an alkanol esterified wax;
    b) mixing the alkanol esterified wax in an amount from about 1 to about 99 wt. % with a colorant to form a homogeneous mixture; and
    c) forming a color mascara composition with the homogeneous mixture from step b).

11. The method according to claim 10 wherein the alkanol esterified wax is behenyl beeswax, hexanediol behenyl beeswax and mixtures thereof.

12. The method according to claim 10 wherein the colorant is selected from the group consisting of iron oxides, ultra marine blue, ferric ammonium ferrocyanide, carmine, manganese violet, ultra marine pink, ultra marine violet, chromium hydroxide green, chromium oxide green, titanium dioxide, organic lakes and mixtures thereof.

13. The method according to claim 10 wherein step c) further comprises selecting an emulsifier from the group of emulsifier components selected from the group consisting of triethanolamine, glyceryl ester an acrylate copolymer, a carboxylic $C_{12}$–$C_{20}$ fatty acid and mixtures thereof.

14. The method according to claim 10 wherein step (c) further comprises selecting a film former from the group consisting of polyvinylpyrolidone, modified polyvinylpyrolidone and mixtures thereof.

* * * * *